United States Patent
Kayton et al.

(10) Patent No.: US 9,839,709 B1
(45) Date of Patent: Dec. 12, 2017

(54) COMPOSITIONS AND METHODS FOR REDUCING OR PREVENTING MEDICAL DEVICE-RELATED INFECTIONS

(71) Applicants: Mark Lawrence Kayton, Tampa, FL (US); Norma Alcantar, Tampa, FL (US); Daniel Restrepo, Tampa, FL (US); Nicholas S. Laconi, Holiday, FL (US); Audrey Lynn Buttice, Palmetto, FL (US); Michael Pierce Ebaugh, Tampa, FL (US)

(72) Inventors: Mark Lawrence Kayton, Tampa, FL (US); Norma Alcantar, Tampa, FL (US); Daniel Restrepo, Tampa, FL (US); Nicholas S. Laconi, Holiday, FL (US); Audrey Lynn Buttice, Palmetto, FL (US); Michael Pierce Ebaugh, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/155,988

(22) Filed: May 16, 2016

Related U.S. Application Data (62) Division of application No. 14/818,772, filed on Aug. 5, 2015, now Pat. No. 9,339,574, which is a division
(Continued)

(51) Int. Cl.
*A61L 2/18* (2006.01)
*A01N 65/08* (2009.01)
(Continued)

(52) U.S. Cl.
CPC ............... *A61L 2/18* (2013.01); *A01N 65/08* (2013.01); *A61L 29/005* (2013.01); *A61L 29/06* (2013.01);
(Continued)

(58) Field of Classification Search
CPC .......... A61L 2/18; A61L 29/005; A61L 29/06; A61L 29/08; A61L 33/0011; A61L 33/18; A01N 65/08
See application file for complete search history.

(56) References Cited

U.S. PATENT DOCUMENTS 6,592,564 B2 7/2003 Finch et al.
6,630,460 B2 10/2003 Koulik
(Continued)

FOREIGN PATENT DOCUMENTS

WO 2004108091 A2 12/2004

OTHER PUBLICATIONS

Melissa Maiefski, et al., "Ethanol lock technique: review of the literature", Infection Control and Hospital Epidemiology, 30(11):1096-1108, 2009.
(Continued)

*Primary Examiner* — Regina M Yoo
(74) *Attorney, Agent, or Firm* — Thomas|Horstemeyer, LLP (57) ABSTRACT

Provided herein is a method of reducing a microbial infection of a heparinized surface wherein heparin precipitation is reduced as compared to a control. In some embodiments a composition comprising ethanol and isopropanol is applied to the surface. In other embodiments, two or more ethanol compositions are applied and removed sequentially from the surface prior to contacting the surface with a biological fluid, tissue or vessel, wherein the composition in each successive administration comprises an increased amount of ethanol. Also provided is a method of reducing a microbial infection of a surface comprising applying a mucilage extract from an *Opuntia ficus indica* species to the surface.

8 Claims, 5 Drawing Sheets

Related U.S. Application Data of application No. 14/056,186, filed on Oct. 17, 2013, now Pat. No. 9,125,959.

(60) Provisional application No. 61/714,932, filed on Oct. 17, 2012.

(51) Int. Cl.
*A61L 33/00* (2006.01)
*A61L 33/18* (2006.01)
*A61L 29/08* (2006.01)
*A61L 29/06* (2006.01)
*A61L 29/00* (2006.01)

(52) U.S. Cl.
CPC ........... *A61L 29/08* (2013.01); *A61L 33/0011* (2013.01); *A61L 33/18* (2013.01); *A61L 2300/404* (2013.01); *A61L 2300/42* (2013.01)

(56) References Cited

U.S. PATENT DOCUMENTS

| | | | |
|---|---|---|---|
| 2004/0091504 A1* | 5/2004 | Hamann | A61K 8/0208 424/195.17 |
| 2004/0091557 A1* | 5/2004 | Hamann | A61K 8/0208 424/727 |
| 2005/0037054 A1* | 2/2005 | Hamann | A41D 19/0058 424/443 |
| 2010/0087788 A1 | 4/2010 | Rosenblatt et al. | |
| 2011/0135720 A1 | 6/2011 | Seabrook, Jr. et al. | |
| 2013/0139283 A1* | 5/2013 | Katzir | A01N 65/08 800/298 |

OTHER PUBLICATIONS

Marcia Pomplun, et al., "Stability of a heparin-free 50% ethanol lock solution for central venous catheters", J Oncol Pharm Pract, 13:33, 2007.

* cited by examiner

FIG. 8

COMPOSITIONS AND METHODS FOR REDUCING OR PREVENTING MEDICAL DEVICE-RELATED INFECTIONS

CROSS REFERENCE TO RELATED APPLICATIONS

This application is a divisional of co-pending U.S. patent application Ser. No. 14/818,772, filed on Aug. 5, 2015, entitled "COMPOSITIONS AND METHODS FOR REDUCING OR PREVENTING MEDICAL DEVICE-RELATED INFECTIONS," the contents of which is incorporated by reference herein in its entirety.

U.S. patent application Ser. No. 14/818,772, filed on Aug. 5, 2015, entitled "COMPOSITIONS AND METHODS FOR REDUCING OR PREVENTING MEDICAL DEVICE-RELATED INFECTIONS," is a divisional application of U.S. patent application Ser. No. 14/056,186, now U.S. Pat. No. 9,125,959, issued on Sep. 8, 2015, having the title "COMPOSITIONS AND METHODS FOR REDUCING OR PREVENTING MEDICAL DEVICE-RELATED INFECTIONS", filed on Oct. 17, 2013, which claims the benefit of U.S. Provisional Patent Application Ser. No. 61/714,932 filed on Oct. 17, 2012, the contents of which are incorporated by reference here in their entirety.

BACKGROUND

Since the 1973 description by Broviac of his use of the silicone catheter that now bears his name [Broviac J W, et al., Surg Gynecol Obstet 136:602-606, 1973], tunneled central venous catheters and ports have played pivotal roles in making advances in survival possible for children with cancer and for those requiring hyperalimentation, hemodialysis, or exchange transfusion. Although surgically-implanted vascular catheters have been essential in enabling the care of such children, our patients continue—even in 2012—to be vexed by catheter-related bloodstream infections. In pediatric oncology, catheter-related bloodstream infections remain the most common cause of nosocomial infection [Simon A., et al., Infect Control Hosp Epidemiol 21:592-6, 2000]. Following the recent declaration by the Centers for Medicaid Services that hospital-acquired catheter-related bloodstream infections may result in reductions or elimination of reimbursement to hospitals [Federal Register, available at www.federalregister.gov/articles/2011/06/06/2011-13819/medicaid-program-payment-adjustment-for-provider-preventable-conditions-including-health#p-69, accessed Feb. 26, 2012], the urgency of the problem is now peaking rather than diminishing.

Numerous strategies have been advanced to combat catheter-related bloodstream infections in children, including insertion checklists, which are useful at the time of catheter insertion but do not address decontamination over extended time periods [Pronovost P, et al., N Engl J Med 355:2725-2732, 2006]; instillation of antibiotic-locks, which carry the spectre of fostering resistant organisms [Smith T L, et al.: N Engl J Med 340:493-501, 1999]; and instillation of clot-dissolving substances such as urokinase, which may actually lead to bacteremia [La Quaglia M P, et al., J Pediatr Surg 29(6):742-745, 1994]. To date, no heparin-compatible, prophylactic solution exists that is suitable for pediatric administration and carries both antibacterial and antifungal activities. A promising recent development, however, has been the intraluminal use of ethanol.

Ethanol-locking strategies in pediatrics have gained traction following a 2003 retrospective report by Dannenberg et al. in which 18 pediatric patients with Broviac catheters were treated with a 74% ethanol solution that was allowed to dwell in the catheter lumen for 20-24 hours and then flushed through [Dannenberg C, et al., J Pediatr Hematol Oncol 25(8):616-621, 2003]. This technique appeared to help treat refractory infections and did not seem to cause any symptoms in children. Others went on to find that ethanol did not appear to damage silicone catheters at the concentrations used [Crnich C J, et al., Infect Control Hosp Epidemiol 26:708-714, 2005].

Building on such retrospective reports, one of the present inventors ran the first prospective, pediatric clinical trial to study safety and blood alcohol levels among children receiving ethanol-lock therapy four times a week [Kayton M L, et al., J Pediatr Surg 45:1961-1966, 2010]. Blood alcohol levels were indeed all below the "legal limit" of 80 mg/dL. However, the study was voluntarily terminated after 123 ethanol-lock administrations, but prior to full patient accrual, when an undue incidence of catheter occlusion was noted. This was serious enough in 3 of the 12 patients studied to warrant return to the operating room, including in one patient whose device fractured and embolized after flushing the catheter against a solid obstruction of the lumen. Catheter thrombosis following ethanol-lock administration has been reported in several other trials now that the use of ethanol has become more widespread [Wales P W, et al., J Pediatr Surg 46:951-956, 2011; Mouw E, et al., J Pediatr Surg 43:1025-1029, 2008]. As a result, many pediatric oncologists and surgeons now shy away from ethanol-lock use as prophylaxis, fearing loss of the very catheter they wish to preserve; ethanol-locks are generally used as a late salvage maneuver in the setting of refractory infection.

BRIEF DESCRIPTION OF THE DRAWINGS

FIG. 5 shows aggregation of fluorescence-labelled *E. Coli* with *Opuntia ficus indica* mucilage: (A) control showing *E. Coli*; (B) addition of calcium; (C) addition of 2 ppm of mucilage.

DETAILED DESCRIPTION

Provided herein is a method of reducing a microbial infection of a heparinized surface wherein heparin precipitation is reduced as compared to a control. In some embodiments a composition comprising ethanol and isopropanol is applied to the surface. In other embodiments, two or more ethanol compositions are applied and removed sequentially from the surface prior to contacting the surface with a biological fluid, tissue or vessel, wherein the composition in each successive administration comprises an increased amount of ethanol. Also provided is a method of reducing a microbial infection of a surface comprising, applying a composition comprising a mucilage extract from an *Opuntia ficus indica* species to the surface. Term definitions used in the specification and claims are as follows.

Definitions

As used in the specification and claims, the singular form "a," "an," and "the" include plural references unless the context clearly dictates otherwise.

A "composition" is intended to mean a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative". In some embodiments, the control is a heparinized surface treated with 70% ethanol.

An "effective amount" is an amount sufficient to effect beneficial or desired results. An effective amount can be administered in one or more administrations, applications or dosages.

The term "heparin" refers herein to a sulfated, and in some embodiments, highly sulfated, glycosaminoglycan. In some embodiments, the heparin is derived from mucosal tissues of porcine intestines or bovine lungs. In other embodiments, the heparin is a synthetic heparin. It should be understood that the term "heparin" includes modified and substituted heparin molecules.

The term "heparin precipitation" refers to the formation of a particulate comprising heparin.

The term "heparinized surface" refers herein to a surface to which heparin is bound. It should be understood that the heparin can be bound to the surface in any manner, including via covalent bonding or non-covalent bonding. Some types of non-covalent interactions include hydrogen bonds, ionic bonds, van der Waals forces, and hydrophobic interactions. In some embodiments, fluid-derived heparin is bound to the surface of, for example, a medical device during use of the medical device.

As used herein, the term "mucilage" refers to a composition comprising one or more of arabinose, galactose, rhamnose, and galacturonic acid.

The terms "prevent", "preventing" "prevention" and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms. In some embodiments, the condition is the formation of heparin precipitate.

The terms "subject," "individual," and "patient" are used interchangeably herein and refer to a vertebrate, preferably a mammal, more preferably a human. Mammals include, but are not limited to, murines, simians, humans, farm animals, sport animals, and pets.

DESCRIPTION

Data provided herein indicates that precipitation between ethanol and residual or catheter-bound heparin is likely to account for the observed adverse events associated with ethanol-locks of catheters. Heparin is known to become sequestered on silicone membranes [Mehta N M, et al., Intens Care Med 33:1018-1024, 2007], and since most vascular access devices in current use are silicone, it is likely that residual or catheter-bound heparin remains present even after vigorous flushing. This may be the Achilles' heel that renders 70% ethanol unsafe for widespread use among children with mediports, as precipitation is reliably observed between 70% ethanol and 100 units/mL heparin. Conceding that heparin is going to be ubiquitous in the vascular catheters of children, and that an anti-infective solution must therefore be heparin-compatible, provided herein is a three-pronged approach to this problem: (1) evaluating novel combinations of alcohols as solvents, (2) evaluating alternative methods of delivery for 70% ethanol, and (3) looking for alternative agents altogether. As an alternative agent, the present disclosure focuses upon a renewable natural substance that shows bacterial-binding capability for purification of drinking water in the developing world; namely, the "mucilage" component of the Mexican cactus *Opuntia ficus indica* [Buttice A L, et al., Environ Sci Technol 44:3514-3519, 2010].

The first approach includes using turbidimetry, particle size evaluation, and infrared spectroscopy to find an ideal "triple point" at which ethanol, isopropanol, and heparin are compatible in solution, and at which particle size of any minimal precipitant that may be present is minimized. The second approach includes validation of a laboratory model simulating heparin adsorption and retention on a surface and use of this model to show that delivery of sequentially-escalating concentrations of ethanol will result in less precipitate formation in a heparin-containing system than will one-time delivery of 70% ethanol into that system. The third approach includes use of mucilage extracted from *Opuntia ficus indica*, at concentrations from approximately 1-10 parts per million (ppm), to show that the mucilage (a) is compatible with heparin, and (b) will exhibit nonspecific binding and aggregation of microorganisms in the presence of heparin.

Accordingly, provided herein is a method of reducing a microbial infection of a heparinized surface wherein heparin precipitation is reduced as compared to a control. In some embodiments a composition comprising ethanol and isopropanol is applied to the surface. In other embodiments, two or more ethanol compositions are applied and removed sequentially from the surface prior to contacting the surface with a biological fluid, tissue or vessel, wherein the composition in each successive administration comprises an increased amount of ethanol. In some embodiments, the control is a heparinized surface to which 70% ethanol has been applied.

Accordingly, provided herein is a method of reducing microbial infection of a heparinized surface comprising, applying a composition of ethanol and isopropanol to the surface and subsequently removing the composition, wherein the ethanol and isopropanol together comprise approximately 70% of the composition, and wherein heparin precipitation is reduced as compared to a control. The term "heparinized surface" refers herein to a surface to which heparin is bound. It should be understood that the heparin can be bound to the surface in any manner, including via covalent bonding or non-covalent bonding. Some types of non-covalent interactions include hydrogen bonds, ionic bonds, van der Waals forces, and hydrophobic interactions. In some embodiments, fluid-derived heparin is bound to the surface of, for example, a medical device during use of the medical device. In other embodiments, the heparinized surface is coated with a heparin prior to use.

In some embodiments, the ethanol and the isopropanol each comprise approximately 35% of a solution. In other embodiments, the ethanol and isopropanol comprise approximately 10% and 60%, 20% and 50%, 30% and 40%, 40% and 30%, 50% and 20%, or 60% and 10%, respectively, of the solution. The surfaces described herein can be treated with the ethanol and isopropanol compositions for any amount of time. These treatments, or applications, can be performed in any manner, including, but not limited to, filling an interior lumen of a medical device with the ethanol and isopropanol solution, and dipping a medical device (wholly or partially) into the ethanol and isopropanol solution. In some embodiments, the surfaces are treated with an ethanol and isopropanol composition for one to ten seconds, one to ten minutes, one to ten hours, or up to or exceeding 24 hours. In some embodiments, the surfaces are treated prior to use of a medical device comprising the surfaces. In other embodiments, the surfaces are treated during use of a medical device comprising the surfaces. "Use" of a medical device includes placement of the medical device within a subject, either wholly or partially.

It should be understood that the surface of any embodiment disclosed herein can be contained within or be a part of any medical device. In one embodiment, the medical device is a catheter. It should be further understood that the surface can comprise any material appropriate for the making of a medical device. In one embodiment, the surface comprises silicone.

As used herein, the term "microbe" includes a bacterium, virus, fungus, yeast, and the like. Bacteria may be those of any genus and species, including but not limited to, *Escherichia coli*, and a *Staphylococcus* species such as *Staphylococcus aureus*. "Reducing a microbial infection" includes a reduction in the number or viability of microbes present on a surface as compared to a control. In these embodiments, a control can be an untreated surface.

Also provided herein is a method of reducing a microbial infection on a heparinized surface comprising, sequentially applying two or more ethanol compositions to the surface and removing each solution prior to applying a subsequent ethanol composition or prior to contacting the surface with a biological fluid, tissue or vessel, wherein the ethanol composition in each successive application comprises an increased amount of ethanol, and wherein heparin precipitation is reduced as compared to a control. Two, three, four, five or six applications are included herein. In one embodiment three ethanol solutions are applied. These methods preferably reduce the amount of heparin precipitation once a medical device comprising the surface is in use (as compared to a medical device treated with a single 70% ethanol solution).

The ethanol compositions described herein can comprise any amount of ethanol, and in some embodiments, the two or more ethanol compositions each comprise approximately 70% or less ethanol. In one embodiment, a first ethanol composition comprises approximately 30% ethanol, a second ethanol composition comprises approximately 50% ethanol, and a third ethanol composition comprises approximately 70% ethanol.

Also provided herein is a method of reducing a microbial infection on a heparinized surface comprising, sequentially applying two or more alcohol compositions to the surface and removing each composition prior to applying a subsequent alcohol composition or prior to contacting the surface with a biological fluid, tissue or vessel, wherein the composition in each successive application comprises an increased amount of alcohol, and wherein heparin precipitation is reduced as compared to a control. Each alcohol composition can comprise any combination of alcohols including ethanol and isopropanol. For example, in one embodiment, a first alcohol solution comprises approximately 30% of any combination of alcohols, a second alcohol solution comprises approximately 50% of any combination of alcohols, and a third alcohol solution comprises approximately 70% any combination of alcohols.

The surfaces described herein can be treated with two or more ethanol or alcohol compositions for any amount of time. These treatments, or applications, can be performed in any manner, including, but not limited to, filling an interior lumen of a medical device with an alcohol solution, and dipping a medical device (wholly or partially) into an alcohol solution. In some embodiments, the surfaces are treated with each ethanol or alcohol solution for one to ten seconds, one to ten minutes, one to ten hours, or up to or exceeding 24 hours. In some embodiments, the surfaces are treated prior to use of a medical device comprising the surfaces. In other embodiments, the surfaces are treated during use of a medical device comprising the surfaces. "Use" of a medical device includes placement of the medical device within a subject, either wholly or partially.

Further provided herein is a method of reducing a microbial infection of a heparinized surface comprising, applying a composition comprising a mucilage extract from an *Opuntia ficus indica* species to the surface. In some embodiments, heparin precipitation is reduced as compared to a control. One, two, three, four, five, six or more applications are included herein.

*Opuntia ficus indica* belongs to the Cactaceae family, from arid and semiarid regions that grow in the form of shrub or tree up to 5 m tall. This species is native from Mexico, but it was later introduced into Southern Europe, Africa, and India. The mucilage extracted from the cladodes of *Opuntia* sp. contains polygalacturonic acid (very similar to pectin structure), plus residues of some sugars, such as D-galactose, D-xylose, L-arabinose, L-rhamnose and D-galacturonic acid. Accordingly, as used herein, the term "Opuntia ficus indica mucilage" refers to a composition comprising one or more of arabinose, galactose, rhamnose, xylose, and polygalacturonic acid. In some embodiments, the mucilage extract is at a concentration between approximately 1-30 ppm, 1-20 ppm, 1-15 ppm, or 1-10 ppm.

It should be understood that the Opuntia ficus indica mucilage can be isolated via any means known to those of skill in the art. For example, the mucilage can isolated using one of the following methods, or its equivalent.

Method 1: Opuntia cladodes without any spines (2.5 kg) are washed repeatedly with tap water. Mucilage is produced by boiling the cladodes cut in small pieces in water (2 L) until the material is light green and soft (20 minutes). Cladode pieces are separated from the mucilage solution using a large-pore sieve. Total solids (TS) and volatile solids (VS) are determined and VS is used to calculate mucilage concentration. This product is a liquid.

Method 2: 2.5 kg of Opuntia cladodes are boiled with 2 L of water as previously described, but the mucilage produced is dried in a fluidized dryer (Buchi Mini spray-dryer B-209). Drying conditions are the following: inlet temperature, 130° C.; outlet temperature, 77° C.; aspirator, 100%. Solution was fed at 3 ml/min approximately (All process lasted 3.5 h). The product is separated from the glass chamber and kept in a closed flask at ambient temperature before other assessments are applied to the sample. This product is a powder.

Method 3: 2.3 kg of fresh Opuntia cladodes are cut in large strips and passed through a commercial fruits/vegetables extractor. The green, viscous mucilage obtained is centrifuged in Falcon tubes (50 ml) during one hour approximately at 6000 rpm. The green pellet is discharged and the mucilage (quite transparent) is dried as previously described. This product is a powder.

As noted above, the "heparinized surface" to which the Opuntia ficus-indica mucilage is applied can be any surface to which heparin is bound. It should be understood that the heparin can be bound to the surface in any manner, including via covalent bonding or non-covalent bonding. Some types of non-covalent interactions include hydrogen bonds, ionic bonds, van der Waals forces, and hydrophobic interactions. In some embodiments, fluid-derived heparin is bound to the surface of, for example, a medical device during use of the medical device. In other embodiments, the heparinized surface is coated with a heparin prior to use.

The surfaces described herein can be treated with a composition comprising an Opuntia ficus-indica mucilage for any amount of time. These treatments, or applications, can be performed in any manner, including, but not limited to, filling an interior lumen of a medical device with a composition comprising a mucilage extract, and dipping a medical device (wholly or partially) into a composition comprising a mucilage extract. In some embodiments, the surfaces are treated with a composition comprising a mucilage extract for one to ten seconds, one to ten minutes, one to ten hours, or up to or exceeding 24 hours. In some embodiments, the surfaces are treated prior to use of a medical device comprising the surfaces. In other embodiments, the surfaces are treated during use of a medical device comprising the surfaces. "Use" of a medical device includes placement of the medical device within a subject, either wholly or partially.

It should be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. All patents, patent applications, and publications referenced herein are incorporated by reference in their entirety for all purposes.

EXAMPLES

Example 1

Heparin Precipitate Formation Varies Upon Incubation with Different Percentages of Ethanol Methods It was shown that precipitation of heparin with ethanol is concentration-dependent, and increases exponentially when the heparin concentration is raised from 10 units/mL, as is used for Broviac catheters, to 100 units/mL, as is used by most centers in mediports. To demonstrate this, 70% ethanol was incubated with either 0, 1, 10, or 100 units of heparin overnight at the temperatures depicted in FIG. 1, and measured resultant precipitate by turbidimetry (Micro 100 turbidimeter, HF Scientific, Inc.). At all temperature conditions, 70% ethanol reliably formed several thousand-fold more precipitate with 100 units/mL heparin than it did with lower heparin concentrations (results expressed on logarithmic scale in FIG. 1; statistical analysis by ANOVA and post-hoc T testing with Bonferroni correction for multiple comparisons; $p<0.05$ for 100 units/mL heparin vs. other concentrations; * denotes $p<0.05$).

Figure 2:
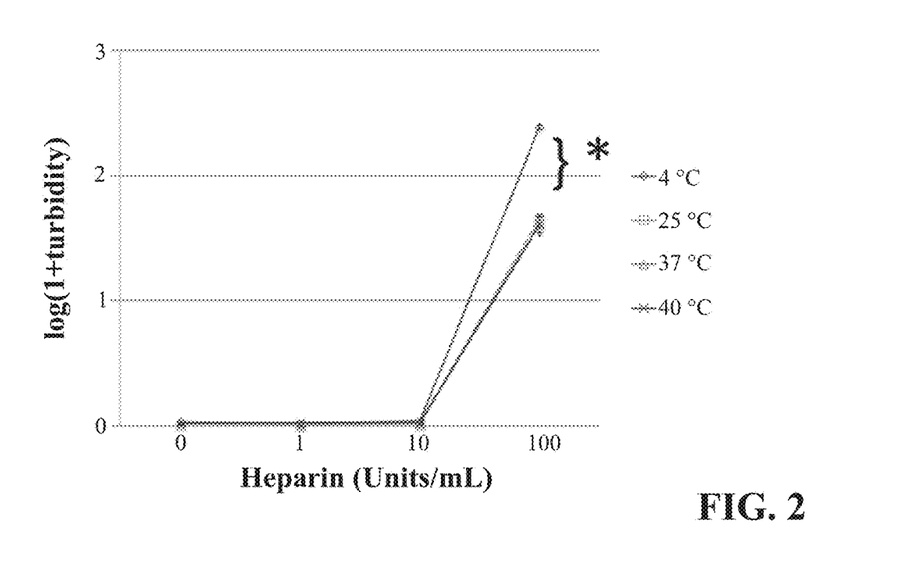
FIG. 2 is a graph showing the results of incubation of 50% ethanol with either 0, 1, 10, or 100 units of heparin overnight at the temperatures depicted (* denotes $p<0.05$).
Figure 3:
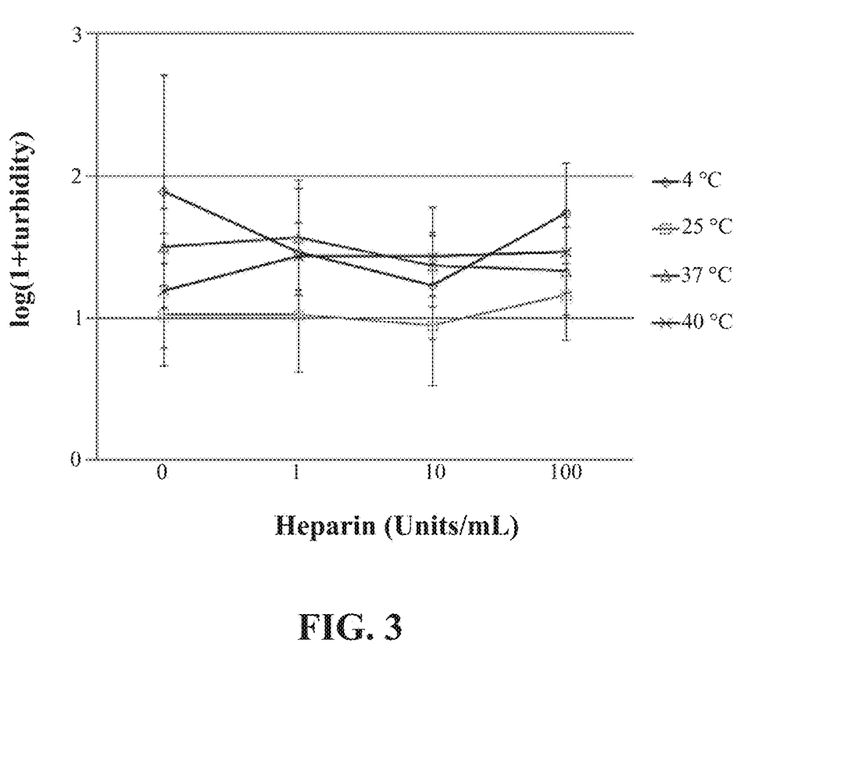
FIG. 3 is a graph showing the results of incubation of 30% ethanol with either 0, 1, 10, or 100 units of heparin overnight at the temperatures depicted.

Heparin (range, 0-100 units/mL) was then incubated overnight with 50% or 30% ethanol. Precipitation was measured in nephelometric turbidity units (NTU's) at 4-40° C. (Micro 100 turbidimeter, HF Scientific, Inc.; n=6 samples per condition). Means were compared by analysis of variance (ANOVA) with post-hoc T-test using Bonferroni correction and $p<0.05$ considered significant. FIGS. 2 and 3 below show the results (wherein * denotes $p<0.05$).

Results

Figure 1:
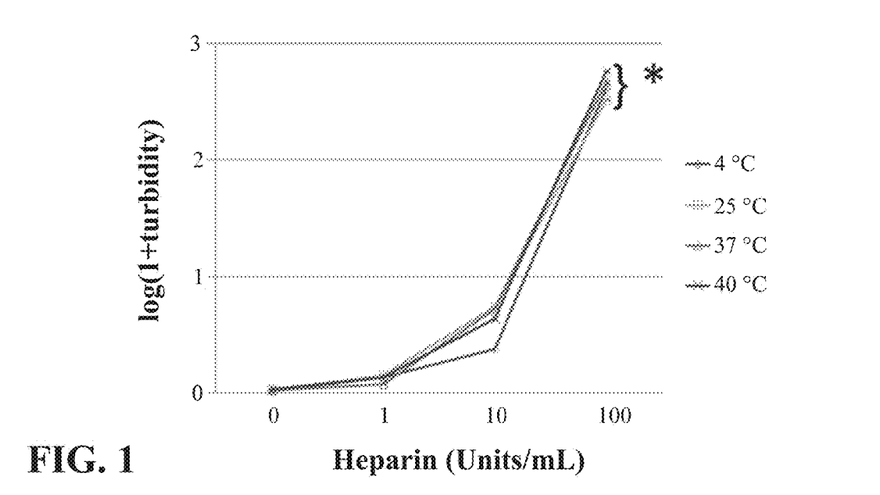
FIG. 1 is a graph showing the results of incubation of 70% ethanol with either 0, 1, 10, or 100 units of heparin overnight at the temperatures depicted (* denotes $p<0.05$).

Heparin and ethanol formed dose-dependent precipitate, which is shown for heparin with 70% ethanol in FIG. 1 above and Table 1 below. Solutions of 50% and 70% ethanol resulted in exponentially more precipitate with 100 units/mL heparin than with lower heparin concentrations ($p<0.05$), but 30% ethanol did not precipitate significantly with heparin (FIGS. 1, 2 and 3).

TABLE 1

Precipitation, in NTU's, of heparin in 70% ethanol

|  | 0 Heparin (control) | 1 unit/mL Heparin | 10 units/mL Heparin | 100 units/mL Heparin |
| --- | --- | --- | --- | --- |
| 4 °C. | 0.03 ± 0.01 | 0.36 ± 0.09 | 1.38 ± 0.10 | 410.67 ± 6.92* |
| 25 °C. | 0.05 ± 0.01 | 0.40 ± 0.01 | 4.50 ± 0.03 | 328.00 ± 6.10* |
| 37°C. | 0.05 ± 0.02 | 0.19 ± 0.01 | 4.27 ± 0.01 | 467.83 ± 11.74* |
| 40 °C. | 0.06 ± 0.01 | 0.36 ± 0.02 | 3.33 ± 0.02 | 574.83 ± 8.66* |

(*denotes $p < 0.05$)

Conclusions

Heparin and ethanol, if mixed, exhibit concentration-dependent, exponentially-increasing precipitation. When exposed to a 70% ethanol-locking solution, heparin at 100 units/mL forms over 6,000-fold more precipitate than control, which may explain why catheter occlusion has been observed in patients with mediports receiving ethanol-locks. These observations should help to guide the development of improved locking solutions for prophylaxis and treatment of catheter-related bloodstream infections in pediatrics.

Example 2

Exposure of Heparin to a Combination of Alcohols Totaling 70%, Results in Less Precipitation as Compared to 70% Ethanol Used Alone as a Solvent Additional data provided herein indicates that the combination of isopropanol and ethanol results in a vastly different solubility profile for heparin than does 70% ethanol alone. In particular, use of 35% ethanol plus 35% isopropanol, instead of 70% ethanol, significantly reduced precipitate formation in the presence of either 10 units/mL of heparin (0.74±0.61 NTU's vs. 8.33±0.19, $p<0.05$) or 100 units/mL of heparin (332.89±12.97 NTU's vs. 526.78±4.97, $p<0.05$).

Figure 4:
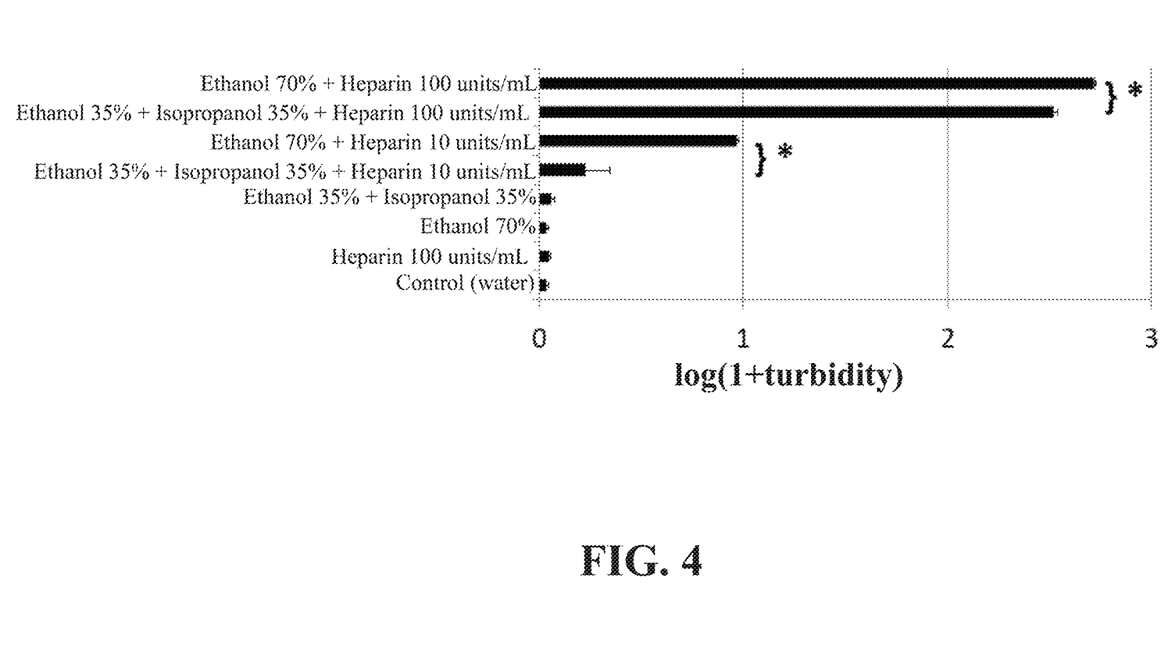
FIG. 4 is a graph showing the results of incubation of 35% ethanol plus 35% isopropanol, instead of 70% ethanol. The figures shows that the ethanol/isopropanol mixtures significantly reduced precipitate formation in the presence of either 10 units/mL of heparin (0.74±0.61 NTU's vs. 8.33±0.19, $p<0.05$) or 100 units/mL of heparin (332.89±12.97 NTU's vs. 526.78±4.97, * denotes $p<0.05$).

These data are depicted in FIG. 4 (wherein * denotes $p<0.05$). When 70% ethanol was mixed with 10 or 100 units/mL of heparin, precipitation reliably occurred. But when the alcohol component was adjusted to 35% ethanol plus 35% isopropanol, and subsequent precipitate formation measured by turbidimetry, less precipitation occurred with the ethanol-isopropanol combination than with ethanol alone, despite the identical overall alcohol content of 70%. Thus, when heparin is exposed to a combination of alcohols totaling 70%, less precipitation results than when 70% ethanol is used alone as a solvent.

Example 3

Optimization of Ethanol/Isopropanol Ratios

To determine the ideally-compatible concentrations of ethanol, isopropanol, and heparin, turbidimetry is further utilized to quantify precipitation; dynamic light scattering to characterize particle size and distribution; and infrared spectroscopy to characterize residual presence or consumption of heparin. Concentration curves are constructed for isopropanol and ethanol in the presence of escalating doses of heparin. Ethanol is evaluated from 0 to 70% in solution, with substitution using escalating concentrations of isopropanol (e.g. 70% ethanol and 0% isopropanol, 65% ethanol and 5% isopropanol, 60% ethanol and 10% isopropanol, and so forth). Each alcohol solution is evaluated for precipitation in the setting of heparin in dosages that are relevant to the amounts present in vascular catheters in clinical practice, ranging from 0-100 units/mL of heparin.

Aliquots of 30 mL are incubated overnight, vortexed, and assessed for precipitation as measured by solution turbidimetry. Turbidimetry includes a measure of the density of particles suspended in solution that can be obtained in liquid phase. The device employed is a bench top turbidimeter (Micro 100 turbidimeter, HF Scientific, Inc). For each ethanol-isopropanol-heparin condition, turbidimetry is determined in nephelometric turbidity units (NTU's) with n=6 to 9 specimens per condition to facilitate statistical analysis. Data are recorded in Microsoft Excel spreadsheets. SAS version 9.2 (SAS Institute, Inc., Cary, N.C.) is used to perform analysis of variance with Bonferroni correction for multiple group wise comparisons, with $p<0.05$ as the threshold for significant differences.

To complement precipitation data, particle size of formed precipitate is determined along the concentration curves described above. This will be accomplished by dynamic light scattering (DLS), which measures the hydrodynamic size of a particle in solution using Brownian motion principles. DLS is performed in triplicate specimens using a Zetasizer Nano-S (Malvern Instruments Corp, Westborough, Mass.). For each sample, following thermal equilibrium a cuvette is filled with 1 mL for each reading. Averages are taken on triplicate readings from each sample. A multimodal algorithm from the manufacturer (Malvern) is used for data fitting, with the hydrodynamic diameter obtained using the Einstein-Stokes equation.

Beyond precipitate amount and particle size, a third important variable concerns the residual activity of heparin in any given alcohol-containing solution. That is, there may exist a threshold alcohol concentration below which heparin retains solubility and activity, but above which heparin is inactivated by precipitation. This has been observed for other chemical species for which a combination of solvents enables solubility that cannot be attained with one solute alone [Israelachvili J, Intermolecular and Surface Forces, Second Ed., (San Diego, Academic Press Ltd., 1995), 38-43]. This would clearly be of interest in the design of an ideal catheter-locking solution.

Accordingly, infrared spectroscopy is used to determine the presence or absence of residual heparin. IR spectroscopy provides a measurement of attenuated total reflection, and in so doing, enables the graphic generation of the molecular "fingerprint" of a substance [Stuart B H, Infrared Spectroscopy: Fundamentals and Application (West Sussex: John Wiley & Sons Ltd., 2004), 33-35]. IR spectra is constructed for heparin controls, ethanol and isopropanol controls, and by comparison and subtraction of spectra it is determined where, along the escalating dosage curves of ethanol and isopropanol, the IR spectroscopic "fingerprint" of native heparin becomes undetectable, indicating loss of all heparin activity owing to precipitation.

Example 4

Compositions and Methods Relating to Sequential Escalation of Ethanol (SEE) or SEE-Locking Provided herein is a strategy called "Sequential Escalation of Ethanol (SEE)," or "SEE-locking". This strategy, detailed below, includes development of a laboratory model for sequestration of heparin on a surface generalizable to a vascular catheter, followed by treatment with gradually-increasing concentrations of ethanol (30%-70%) in order to extract available heparin. This strategy enables the safe delivery of 70% ethanol into the catheter without the formation of clinically significant, heparin-related precipitate.

A laboratory model was developed and validated to simulate the presence of residual or catheter-bound heparin in a vascular access device. Conical falcon tubes were filled with a solution of 100 units/mL heparin. In each tube, either a weight-standardized cellulose sponge or a predetermined number of silicone beads or silicone cubes were suspended. All were evaluated for reproducible sequestration of heparin from solution. To determine which substrate is a better model, either cellulose sponge, silicone beads or silicone cubes were soaked overnight in 100 units/mL heparin based upon prior observations that 70% ethanol and 100 units/mL of heparin rapidly form precipitate that is reproducibly measurable by turbidimetry.

Figure 6:
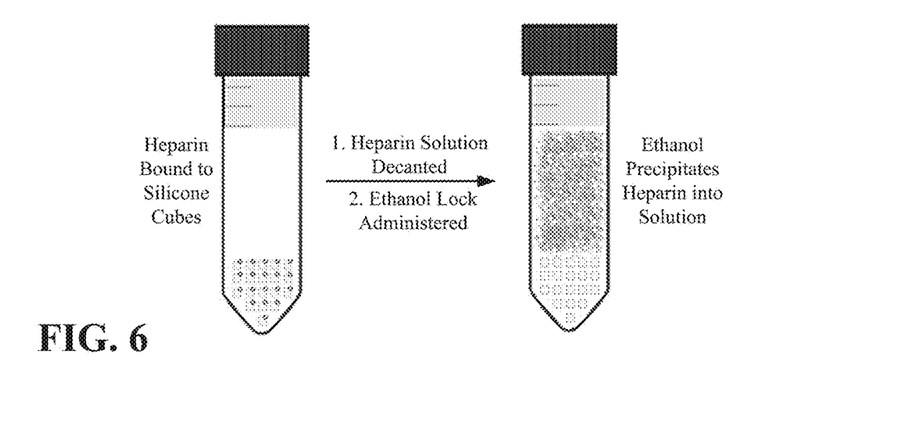
FIG. 6 is a schematic showing a heparin and ethanol incubation procedure.

The next morning, heparin was decanted and replaced with a solution of 70% ethanol. The 70% ethanol was allowed to dwell for four hours with the substrate containing adsorbed heparin. The four-hour dwell was selected based upon experiments showing this to be the minimum time-to-kill for microorganisms adherent to a solid polystyrene surface [Chambers S T, et al., J Hosp Infect 63:193-196, 2006], and therefore, analogous to the environment of a vascular catheter. Following this, ethanol was decanted and precipitation between ethanol and heparin measured in the supernatant by turbidimetry. See FIG. 6. Six replications of each condition were performed. Data were collated on a spreadsheet and graphed by scatterplot.

Figure 7:
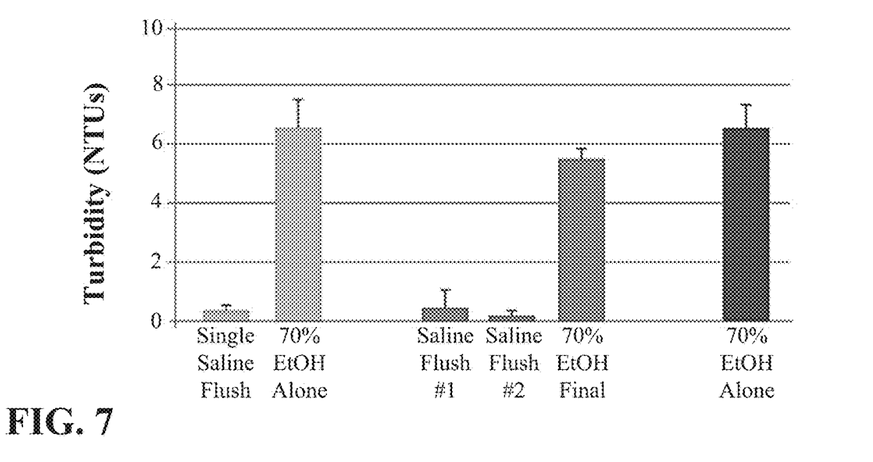
FIG. 7 is a graph showing the results of incubation of heparin with 70% ethanol following no saline flush, a single saline flush, or two saline flushes.

Either cellulose sponge, silicone beads or silicone cubes were then advanced into further experiments, representing the "control" substrate for adsorption of heparin. In the next phase of experiments, it was determined whether residual or adsorbed heparin remains present in the model system, as evidenced by precipitation with 70% ethanol, even after saline rinses. The substrate was again incubated overnight in 100 units/mL heparin. The following day, heparin was decanted and saline rinses employed. Following saline rinses, 70% ethanol was delivered, allowed to dwell for four hours, and precipitation measured, recorded, and analyzed as described above. See FIG. 7.

Figure 8:
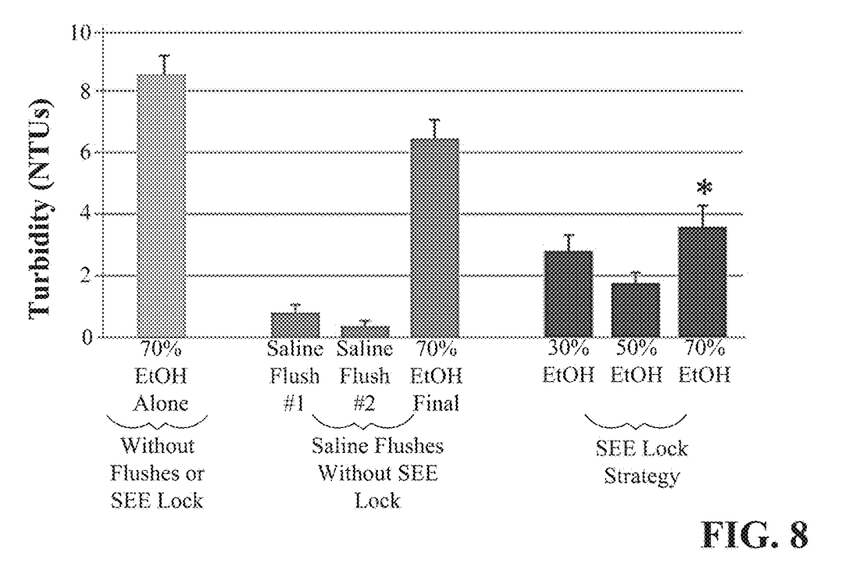
FIG. 8 is a graph showing the results of incubation of heparin with 70% ethanol, 70% ethanol following one or two saline flushes, and a SEE-lock ethanol sequence of 30%, 50% and 70% ethanol.

Testing of sequentially-escalating ethanol concentrations (the SEE-Lock) was then carried out, and compared with the control solution devised above. Parallel groups of 12 tubes were set up, each with cubes. For all groups, the substrate was incubated overnight in 100 units/mL heparin. The next day, substrates were rinsed with either 30% ethanol (or saline for controls), then 50% ethanol (or again saline for controls). All substrates were then treated with 70% ethanol. An additional 12 were treated directly with 70% ethanol without intervening rinse. Cumulative overall and final precipitation amounts were tabulated. The 12 replications of each group (experimental and controls) provided adequate statistical power to determine differences in turbidimetry. Data was compiled and graphed on Microsoft Excel and analyzed by ANOVA using SAS version 9.2 (SAS Institute, Inc., Cary, N.C.). See FIG. 8.

Example 5

Use of a Mucilage Component of the Cactus Species *Opuntia ficus indica* to Bind, Aggregate and Sequester Bacteria The third line of investigation looks beyond ethanol and alcohols altogether in the effort to find alternative, heparin-compatible solutions for catheter locking. The present disclosure demonstrates the ability of the "mucilage" component of the cactus species *Opuntia ficus indica* to bind, aggregate and sequester bacteria. This combination, which principally includes arabinose, galactose, rhamnose, and galacturonic acid [Espino-Diaz M, et al., J Food Sci 75:E347-352, 2010], has been previously studied for medicinal uses [Galati E M, et al., Phytother Res 21:344-346, 2007] and its utility for water purification through its ability to nonspecifically bind microorganisms [Buttice A L, et al., Environ Sci Technol 44:3514-3519, 2010].

Figure 5:
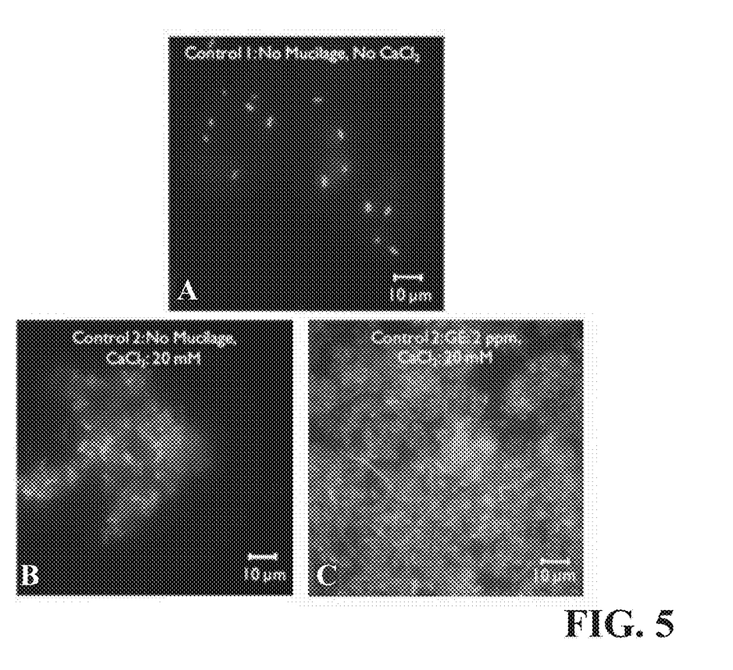
FIG. 5 (A-C) contains images showing that treatment of bacteria in suspension with mucilage at low concentrations (1-10 ppm) resulted in sequestration of microorganisms by aggregation into bacteria-mucilage complexes on the micron scale with bacterial removal rates of 97-98%.

As shown herein, treatment of bacteria in suspension with mucilage at low concentrations (1-10 ppm) resulted in sequestration of microorganisms by aggregation into bacteria-mucilage complexes on the micron scale (FIG. 5) with bacterial removal rates of 97-98%. FIG. 5 shows aggregation of fluorescence-labelled *E. Coli* with *Opuntia ficus indica* mucilage: (A) control showing *E. Coli*; (B) addition of calcium; (C) addition of 2 ppm of mucilage. To date, no one has interrogated the ability of mucilage to aggregate bacteria in a heparin-rich environment such as that found in a biomedical device.

In further experiments, cactus pads are obtained from *Opuntia ficus indica* that are originally purchased form Living Stones Nursery in Tucson, Ariz., and replanted and cultivated in Tampa, Fla. Mucilage is purified as described elsewhere [Buttice A L, et al., Environ Sci Technol 44:3514-3519, 2010], prepared and stored in stock concentrations of 500 ppm. Dilution curves are prepared using escalating dosages of mucilage (0-10 ppm) together with escalating dosages of heparin (0-100 units/mL). Compatibility in solution for each concentration combination is assessed by turbidimetry (for precipitate formation) and infrared spectroscopy (to detect residual presence or degradation of each component) using techniques analogous to those described above. Compatible concentrations are established for mucilage and heparin, followed by assays of bacterial binding/sequestration as described in more detail below.

Bacterial binding and removal is tested in suspension for mucilage alone (control) and for mucilage in the presence of heparin. *E. coli* and *S. aureus* are cultured overnight on a Gyromax 727 orbital incubator shaker (Amerex Instruments, Inc.) at 35° C. and 200 rpm. Initial counts of bacteria are made using a cell counting chamber. Bacteria are washed, pelleted by centrifugation and resuspended, and loaded into 10 mL columns at a bacterial concentration of 108 cells/mL. At this concentration visible time-to-settling with mucilage in the presence of calcium is measured by simple timer; mucilage has previously been shown to induce bacterial aggregation and settling in column assays faster than control specimens without mucilage. Similar results are obtained in the presence of heparin.

To confirm sequestration of bacteria by mucilage or by mucilage plus heparin, 1 mL samples are taken from the tops of each column and final bacterial cell counts evaluated using standard microbiology plate counting techniques on bacterial growth media. The resulting counts are compared with the initial bacterial concentrations, and a removal ratio obtained. Thus both time-to-aggregation and overall ratio of bacteria in each column are obtained for both the mucilage-only group and the mucilage plus heparin group. Resultant differences are compared for the mucilage-only group and the mucilage plus heparin group using Student's T-test for the two conditions at each concentration tested. Each condition is replicated 20-fold to minimize the risk of type II error. These experiments demonstrate the applicability of mucilage for future clinical trials as a decontaminating agent for central venous catheters.

The invention claimed is:

1. A method of reducing a microbial infection of a heparinized surface, comprising: applying a composition comprising a mucilage extract from an *Opuntia ficus indica* species to the heparinized surface.

2. The method of claim 1, wherein the mucilage extract is at a concentration between approximately 1-10 ppm.

3. The method of claim 1, wherein a medical device comprises the heparinized surface.

4. The method of claim 3, wherein the medical device is a catheter.

5. The method of claim 1, wherein the heparinized surface comprises a silicone.

6. The method of claim 1, wherein the microbial infection is caused by *E. coli*.

7. The method of claim 1, wherein the microbial infection is caused by *S. aureus*.

8. The method of claim 1, wherein the microbial infection is reduced by at least 97%.

\* \* \* \* \*